United States Patent [19]

Böhner et al.

[11] Patent Number: 4,957,535
[45] Date of Patent: Sep. 18, 1990

[54] NOVEL ANNULARLY-LINKED TRIAZOLE COMPOUNDS

[75] Inventors: Beat Böhner, Binningen, Switzerland; Georg Pissiotass, Lörrach, Fed. Rep. of Germany; Hans Moser, Magden, Switzerland

[73] Assignee: Ciba-Geigy Corporation, Ardsley, N.Y.

[21] Appl. No.: 250,888

[22] Filed: Sep. 29, 1988

Related U.S. Application Data

[63] Continuation-in-part of Ser. No. 886,501, Jul. 17, 1986, Pat. No. 4,789,394.

[51] Int. Cl.$^5$ .................. A01N 43/90; C07D 513/04
[52] U.S. Cl. ........................... 71/76; 71/91; 540/545
[58] Field of Search .............. 71/76, 91; 540/545

[56] References Cited

U.S. PATENT DOCUMENTS

| | | | |
|---|---|---|---|
| 4,066,437 | 1/1978 | von Bredow et al. | 71/91 |
| 4,437,877 | 3/1984 | Nagano et al. | 71/91 |
| 4,561,880 | 12/1985 | Shimano et al. | 71/92 |

Primary Examiner—Glennon H. Hollrah
Assistant Examiner—Patricia L. Morris
Attorney, Agent, or Firm—Kevin T. Mansfield; Edward McC. Roberts

[57] ABSTRACT

Novel bicyclic triazole compounds of the formula I have an excellent herbicidal and plant-growth regulating action.

The compounds correspond to the formula I

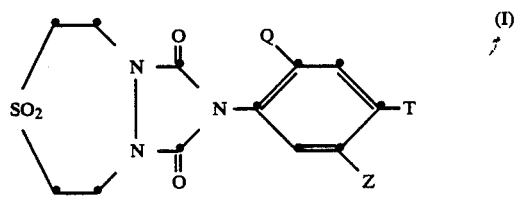

wherein
Q is hydrogen or halogen,
T is halogen, and
Z is a radical —XR or —COXR, in which
X is oxygen, sulfur or a radical —NR$_2$—,
R is hydrogen, a C$_1$–C$_6$-alkyl, C$_3$–C$_6$-cycloalkyl, C$_2$–C$_6$-alkenyl or C$_3$–C$_6$-alkynyl radical, which is unsubstituted or substituted by halogen, or is a radical —A—COXR$_1$, in which
A is a C$_1$–C$_4$-alkylene bridge and
R$_1$ is hydrogen or C$_1$–C$_4$-alkyl, C$_3$–C$_6$-cycloalkyl, C$_3$–C$_4$-alkenyl or C$_3$–C$_4$-alkynyl.

11 Claims, No Drawings

NOVEL ANNULARLY-LINKED TRIAZOLE COMPOUNDS

CROSS-REFERENCE TO RELATED APPLICATION

This is a continuation-in-part of our application Ser. No. 886,501, filed July 17, 1986, now U.S. Pat. No. 4,789,394.

The present invention relates to novel annularly-linked triazole compounds of the formula I given below, which have an herbicidal action and an action regulating plant growth, and to the production of these novel compounds. The invention relates also to compositions containing the novel compounds, and to the use thereof for the selective control of weeds or for the regulation of plant growth.

The novel annularly-linked triazole compounds correspond to the formula I

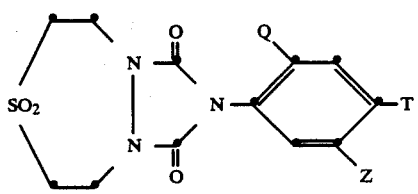

wherein
 Q is hydrogen or halogen,
 T is halogen, and
 Z is a radical —XR or —COXR, in which
  X is oxygen, sulfur or the radical —NR$_1$—,
  R is hydrogen, a C$_1$–C$_6$-alkyl, C$_3$–C$_6$-cycloalkyl, C$_2$–C$_6$-alkenyl or C$_3$–C$_6$-alkynyl radical, which is unsubstituted or substituted by halogen, or is a radical —A—COXR$_1$, in which
   A is a C$_1$–C$_4$-alkylene bridge and
   R$_1$ is hydrogen or C$_1$–C$_4$-alkyl, C$_3$–C$_6$-cycloalkyl, C$_3$–C$_4$-alkenyl or C$_3$–C$_4$-alkynyl.

By halogen in the formula I is meant fluorine, chlorine, bromine or iodine. In the case of the substituent T, chlorine and bromine are preferred.

The term 'alkyl' on its own or as part of another substituent embraces both branched-chain and straight-chain alkyl groups. Examples are: methyl, ethyl, n-propyl, isopropyl, n-butyl, isobutyl, sec-butyl, tert-butyl, n-pentyl, isopentyl, neopentyl and also hexyl with the isomers thereof.

The alkenyl and alkynyl radicals can likewise be branched-chain or straight-chain, and contain preferably 2–6 carbon atoms. Examples are: allyl, methallyl, butenyl, butadienyl, methylbutenyl, dimethylbutenyl, pentenyl, hexenyl, pentenedienyl and hexenedienyl, butyne, methylbutyne, pentyne, hexyne and dimethylbutyne.

The alkenyl bridge corresponding to the radical A can be straight-chain or branched-chain. It can be for example methylene, ethylene, 1-methylmethylene, 1,1-dimethylethylene, 1- or 2-methylethylene, 1,2-dimethylethylene, 1,1- or 2,2-dimethylethylene, propylene or butylene.

The compounds of the formula I have an action regulating plant growth, and can be used for reducing vegetative growth.

The compounds of the formula I have however in particular herbicidal activity, and are suitable for the control of weeds, especially dicotyledonous weeds. It has been shown that with these compounds it is possible to destroy otherwise very resistant problem weeds of the Galium family: bedstraw plants, for example *Galium verum*, yellow galium, *Galium aparine*, goose grass, *Galium mollugo*, common bedstraw, and so forth, against which other known herbicides are frequently inadequately effective.

A great advantage in this respect is that the novel compounds of the formula I behave towards many cultivated plants, such as cereals, maize, rice and also rapeseed, in a selective manner, and can thus be employed for controlling weeds in such crops.

The active substances of the formula I are as a rule successfully applied in amounts of 0.005 to 4 kg per hectare, especially 0.001 to 1 kg per hectare.

In lower applied amounts, the compounds of the formula I are distinguished by good selective growth-inhibiting and selective herbicidal properties, which render them excellently suitable for use in crops of cultivated plants, especially in crops of cereals, cotton, soya-bean, maize and rice. It is also possible in some cases to destroy weeds which could be dealt with hitherto only by the application of total herbicides.

The mode of action of these active substances is unusual. Many are capable of being translocated, that is to say, they are taken up by the plants and transported to other locations, where they produce the desired effect. It is thus possible for example by surface treatment of perennial weeds to destroy them at the roots. The novel compounds of the formula I are effective in applied amounts which are very small compared with the amounts required to obtain the same effect using other herbicides and plant-growth regulators.

9-Aryl-8,10-dioxo-4,1,7,9-thiatriazabicyclo[5.3.0]-decane-4,4-dioxides are already known as being herbicides from the German Offenlegungsschrift No. 2,638,543.

It has now been found that, surprisingly, the novel compounds of the formula I of the present invention have properties which are considerably better than those of the prior known compounds. With the novel compounds of the formula I, the amount of active substance per hectare can be drastically reduced, a factor which is of advantage both ecologically and economically.

Novel annularly-linked 1-phenyl-2,5-dioxo-1H-1,3,4-triazole compounds of the formula I exhibiting a good action are those wherein
 Q is hydrogen or fluorine,
 T is fluorine, chlorine or bromine, and
 Z has the meaning defined under the formula I;
particularly the compounds in which
 Q is hydrogen or fluorine,
 T is chlorine or bromine,
 Z is a radical —XR or —COXR,
 X is oxygen, sulfur or the radical —NR$_1$—,
 R is hydrogen, C$_1$–C$_4$-alkyl, C$_3$–C$_6$-cycloalkyl, C$_3$–C$_6$-alkenyl or C$_3$–C$_6$-alkynyl, and
 R$_1$ is hydrogen or C$_1$–C$_4$-alkyl, C$_3$–C$_6$-cycloalkyl, C$_3$–C$_4$-alkenyl or C$_3$–C$_4$-alkynyl A good action is exhibited likewise by the compounds formula I in which
 Q is hydrogen or fluorine,
 T is chlorine or bromine,
 Z is a radical —XR,
 X is oxygen or sulfur, R is hydrogen, a , $C_{13}$–$C_6$-alkyl, $C_3$–$C_6$-cycloalkyl, $C_3$–$C_6$-alkenyl or $C_3$–$C_6$-alkynyl radical, which is unsubstituted or substituted by halogen;
also by those compounds in which
Q is hydrogen or fluorine,
T is chlorine or bromine,
Z is a radical —XR,
X is a radical —$NR_1$—,
R is hydrogen, $C_1$–$C_6$-alkyl, $C_3$–$C_6$-cycloalkyl, $C_3$–$C_6$-alkenyl or $C_3$–$C_6$-alkynyl, and
$R_1$ is hydrogen, $C_1$–$C_4$-alkyl, $C_3$–$C_6$-cycloalkyl, $C_3$–$C_4$-alkenyl or $C_3$–$C_4$-alkynyl.

A good action is exhibited also by the compounds of the formula I wherein
Q is hydrogen or fluorine,
T is chlorine or bromine,
Z is a radical —COXR,
X is oxygen or sulfur,
R is hydrogen, $C_1$–$C_6$-alkyl, $C_3$–$C_6$-cycloalkyl, $C_3$–$C_6$-alkenyl or $C_3$–$C_6$-alkynyl;
and moreover by those compounds of the formula I in which
T is chlorine or bromine,
Q is hydrogen or fluorine,
Z is a radical —XR,
R is a radical —A—$COXR_1$,
A is a $C_1$–$C_4$-alkylene chain,
X is oxygen or sulfur, and
$R_1$ is hydrogen, $C_1$–$C_6$-alkyl, $C_3$–$C_6$-cycloalkyl, $C_3$–$C_6$-alkenyl or $C_3$–$C_6$-alkynyl;
particularly the compound:
9-(2-fluoro-4-chloro-5-isopropyloxy-phenyl)-8,10-dioxo-4,1,7,9-thiatriabicyclo[5.3.0]-decane-4,4-dioxide.

The compounds of the formula I are produced by reacting a 1-(2-phenyl)-1H-1,3,4-triazolidine-2,5-dione of the formula II

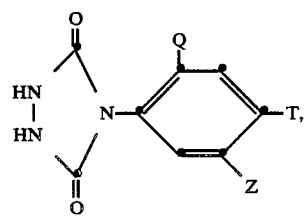

wherein Q, T and Z have the meanings defined under the formula I, in an inert organic solvent at a temperature of 0° to 150° C., in the presence of an amount of base as catalyst, with divinylsulfone ($CH_2$=CH)$SO_2$.

This condensation or addition reaction is best performed in a polar aprotic organic solvent, in the presence of a base as catalyst. Reference is made in this respect to G. Zinner Arch. Pharm. 299 (1966), pp. 312–314, wherein the production of 9-phenyl-8,10-dioxo-4,1,7,9-thiatriazabicyclo[5.3.0]decane-4,4-dioxide is described; or to the German Auslegeschrift No. 2,638,543, in which the production of 9-aryl-8,10-dioxo- or -8-one-10-thione-4,1,7,9-thiatriazabicyclo[5.3.0]decane-4,4-dioxides is described in general.

Polar aprotic organic solvents suitable for this condensation reaction are for example: formamides, aralkylsulfoxides, cyclic ketones, lower alkanols or nitriles.

This condensation or addition reaction is catalysed by the addition of an amount of base, such as alkanolic KOH or NaOH. The temperature for the reaction can vary between 0° and 150° C.

The starting materials of the formula II are for the most part novel. The production of 2-phenyl-1,2,4-triazolidine- 3,5-dione, termed also 4-phenylurazole or N-phenylimide of azodicarboxylic acid, has already been described by J. Thiele, et al., Ann. 283 (1984), p. 1. Further references in this connection are J. Stolle Ber. 45 (1912), p. 273, G. Zinner, et al., Arch. Pharm. 294 (1961), pp. 370–372, and also R.C. Cockson, et al., Tetrahedron Letters 14 (1962), pp. 615–618. The process comprises for example cyclising a 1-ethoxycarbonyl-4-(phenyl)-semicarbazide, $C_2H_5$-O-CO-NH-NH-CO-NH-phenyl, correspondingly substituted in the phenyl nucleus, in a hot alkaline medium; and isolating the 4-(2-phenyl)-1,2,4-triazolidine-3,5-dione from an acid medium, from which it precipitates in crystalline form.

The semicarbazides required for the production of the 1,3,4-triazole-2,5-dione of the formula II and which correspond to the formula III

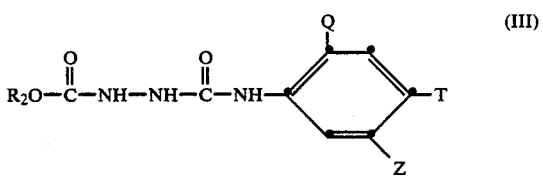

wherein $R_2$ is a $C_1$-$C_6$-alkyl or benzyl radical, and Q, T and Z have the meanings defined under the formula I, can be obtained by reaction of hydrazine hydrate with the equimolar amount of a dialkyl carbonate, and reaction of the formed alkyl carbazate with the equimolar amount of a phenylisocyanate.

The production of the novel annularly-linked triazole compounds of the formula I can be illustrated by the following reaction diagram:

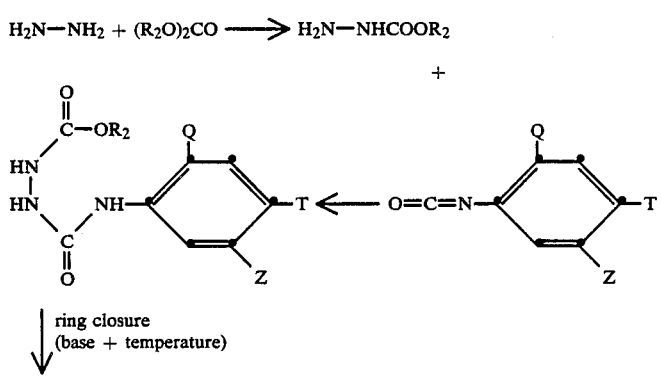

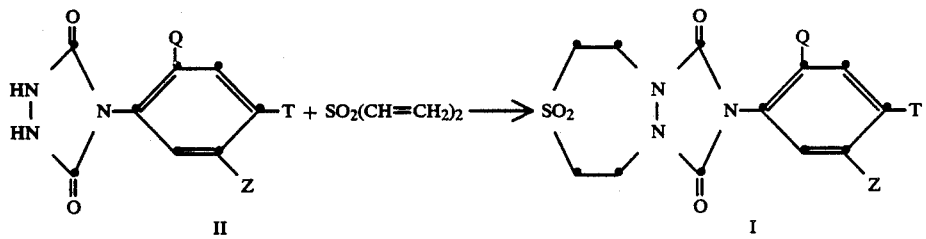

The compounds of the formula I, according to the meaning of Z, can be converted into one another. An important part in this respect is played by the 3-aminoanilidene,9-(3-amino-4-halophenyl)-8,10-dioxo-4,1,7,9-thiatriazabicyclo[5.3.0]decane-4,4-dioxides of the formula Ia. They are obtained by treating a 9-(4-halophenyl)-8,10-dioxo-4,1,7,9-thiatriazabicyclo[5.3.0]-decane-4,4-dioxide with 1 to 1.5 molar equivalents of a nitrating agent, for example fuming nitric acid, or with a mixture of fuming nitric acid and sulfuric acid. The solvent used for the purpose can be concentrated sulfuric acid, and the reaction temperature is to be maintained between −5° and +5° C. The 3-nitroanilide, 9-(3-nitro-4-halophenyl)-8,10-dioxo-4,1,7,9-thiatriazabicyclo[5.3.0]-decane-4,4-dioxide obtained is subsequently reduced to the amine, for example in an inert organic solvent with hydrogen under normal pressure in the presence of Raney nickel, or in water, acetic acid, ethanol or ethyl acetate with 2.5 to 10 molar equivalents of iron filings with at least the equimolar amount of glacial acetic acid at a temperature of 50°–100° C.

These reactions can be illustrated by the following reaction schemes:

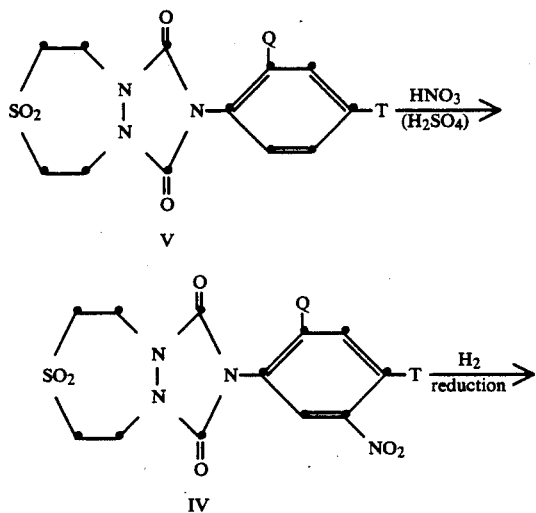

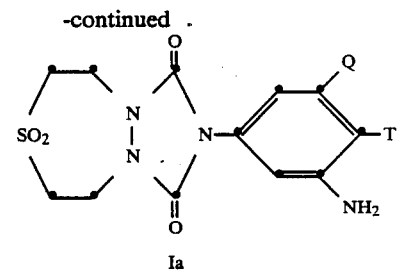

In these formulae, Q and T have the meanings defined under the formula I. The inventive 3-aminoacetanilides of the formula Ia are important key products for the production of further compounds of the formula I. They and the 3-nitroanilides of the formula IV are likewise subject matter of the present invention.

The 3-aminoanilides of the formula Ia can be converted into further compounds of the formula I; for example by treatment with an alkylating agent, such as an alkyl halide or an alkylsulfonic or -arylsulfonic acid, there are obtained the compounds of the formula I in which Z is the amino radical —N(R)R₁.

Furthermore, the 3-aminoanilides of the formula Ia can be converted in an excess of a mineral acid (for example hydrochloric acid or sulfuric acid) with 1–15 molar equivalents of sodium nitrite into the diazonium salt, which is then converted, by decomposition in water or acetic acid, with copper cyanate into the 3-cyanoanilide, 9-(3-cyano-4-halophenyl)-8,10-dioxo-4,1,7,9-thiatriazabicyclo[5.3.0]decane-4,4-dioxide of the formula VI, which for its part is hydrolysed, by boiling with water and the catalytic amount of a base, to the 3-carboxyanilide, 9-(3-carboxy-4-halophenyl)-8,10-dioxo-4,1,7,9-thiatriazabicyclo[5.3.0]decane-4,4-dione of the formula VI. By reaction of this carboxylic ester with a strong halogenating agent, such as phosphorus oxychloride, phosphorus oxybromide, thionyl chloride, thionyl bromide, sulfuryl chloride or bromo succinimide, these is obtained the acid halide of the formula VII, which can be converted, by reaction with an alkanol or thiol of the formula HXR, into a compound of the formula I in which Z is the carbonic acid radical —COXR. These reactions can be illustrated by the following reaction diagram:

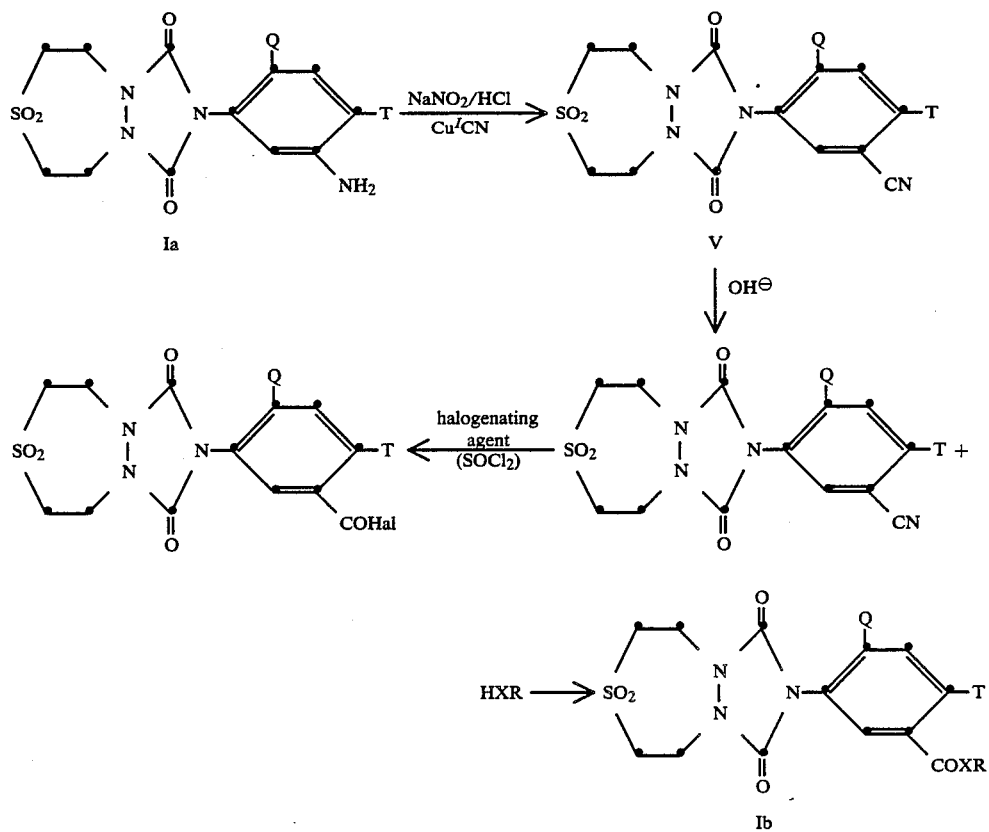

In these formulae, Q, R, T and X have the meanings defined under the formula I.

The diazonium salt produced by reaction of the 3-aminoanilide of the formula Ia with sodium nitrite can be either hydrolysed to the phenol, or converted into a thiophenol or thiophenol derivative, and these derivatives in their turn can be etherified again according to the following reaction diagram:

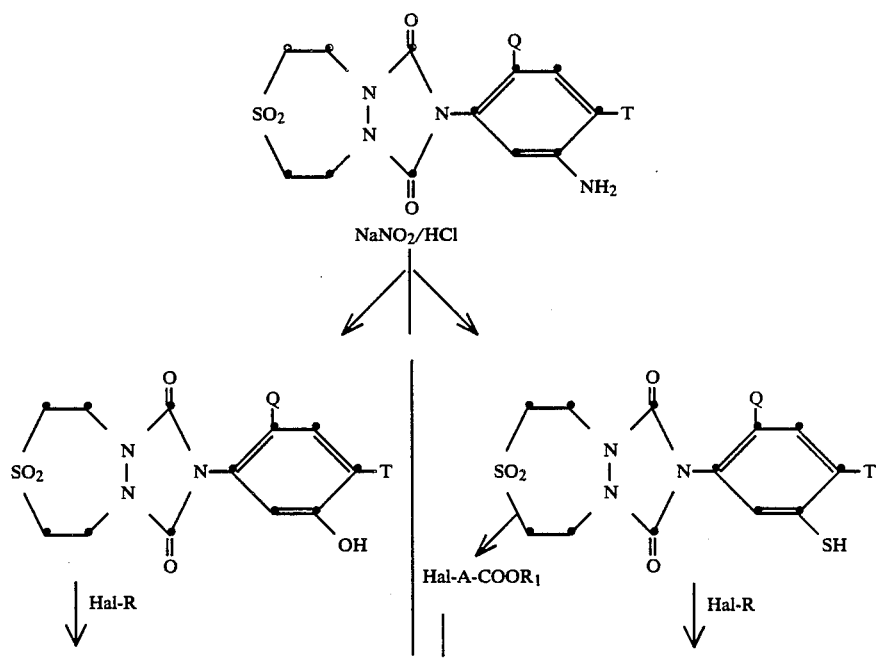

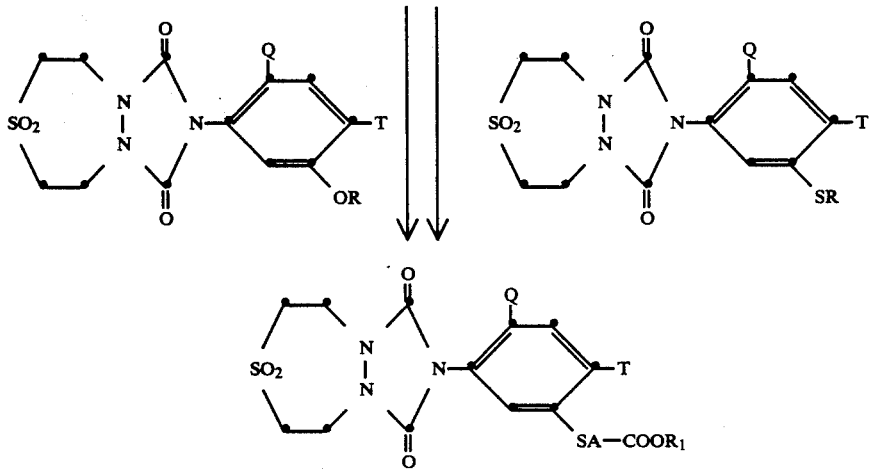

In these formulae, A, Q, R, $R_1$ and T have the meanings defined under the formula I.

The compounds of the formula I have herbicidal properties and also properties enabling plant growth to be greatly reduced. Both monocotyledons and dicotyledons are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

A reduction of the vegetative growth enables in the case of many cultivated plants the growth density to be increased, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

The desiccating and defoliation action of these compounds is used in potato and cotton crops, shortly before they are gathered, in order to render harvesting easier by dessicating undesirable vegetative plant parts.

The compounds of the formula I have however in particular herbicidal activity, and are suitable for the control of weeds, especially dicotyledonous weeds. It has been shown that with these compounds it is possible to destroy otherwise very resistant problem weeds of the Galium family: bedstraw plants, for example *Galium verum*, yellow galium, *Galium aparine*, goose grass, *Galium mollugo*, common bedstraw, and so forth, against which other known herbicides are frequently inadequately effective.

A great advantage in this respect is that the novel compounds of the formula I behave towards many cultivated plants, such as cereals, maize, rice and also rapeseed, in a selective manner, and can thus be employed for controlling weeds in such crops.

The active substances of the formula I are as a rule successfully applied in amounts of 0.005 to 4 kg per hectare, especially 0.001 to 1 kg per hectare.

In lower applied amounts, the compounds of the formula I are distinguished by good selective growth-inhibiting and selective herbicidal properties, which render them excellently suitable for use in crops of cultivated plants, especially in crops of cereals, cotton, soya-bean, maize and rice. It is also possible in some cases to destroy weeds which could be dealt with hitherto only by the application of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at their roots. The novel compounds of the formula I are effective in applied amounts which are very small compared with the amounts required to obtain the same effect using other herbicides and plant-growth regulators.

With larger applied amounts of active substance, all the tested plants are impaired in their development to the extent that they wither.

The present invention relates also to herbicidal and plant-growth-regulating compositions containing a novel active ingredient of the formula I, and also to processes for the pre- and post-emergence controlling of weeds, and for the reduction of growth of monocoteledonous and dicotyledonous plants, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethyl sulfoxide or dimethylformamide, as well as optionally epoxidised vegetable oils, such as epoxidised coconut oil or soyabean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salts of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1979; and Dr. Helmut Stache, "Tenside Taschenbuch", Carl Hanser Verlag, Munich/Vienna, 1981.

The herbicidal preparations contain as a rule 0.1 to 95%, especially 0.1 to 80%, of active ingredient of the formula I, 1 to 99.9% of a solid or liquid additive, and 0 to 25%, particularly 0.1 to 25%, of a tenside.

Preferred formulations are made up in particular as follows: (% =per cent by weight):

Emulsifiable concentrates active ingredient of the formula I: 1 to 20%, preferably 5 to 10%
surface-active agent: 5 to 30%, preferably 10 to 20%
liquid carrier: 50 to 94%, preferably 70 to 85% .

Dusts active ingredient of the formula I: 0.1 to 10%, preferably 0.1 to 1%
solid carrier: 99.9 to 90%, preferably 99.9 to 99% .

Suspension concentrates active ingredient of the formula I: 5 to 75%, preferably 10 to 50%
water: 94 to 25%, preferably 90 to 30%
surface-active agent, 1 to 40%, preferably 2 to 30% .

Wettable powders active ingredient of the formula I: 0.5 to 90%, preferably 1 to 80%
surface-active agent: 0.5 to 20%, preferably 1 to 15%
solid carrier: 5 to 95%, preferably 15 to 90% .

Granulates active-ingredient of the formula I: 0.5 to 30%, preferably 3 to 15%
solid carrier: 99.5 to 70%, preferably 97 to 85% .

Whereas commercial products are preferably in the form of concentrated compositions, the preparations employed by the end-user are as a rule diluted. The preparations can on application be diluted down to 0.001% of active ingredient. The applied amounts are usually 0.005 to 5 kg of active substance per hectare.

The compositions can also contain further additives, such as stabilisers, antifoaming agents, viscosity regulators, binders and adhesives, as well as fertilisers or other active substances for obtaining special effects.

The following Examples illustrate the production of some compounds of the formula I. Further active substances obtained in a corresponding manner are listed in the Tables subsequently given. Temperatures are given in degrees Centigrade and pressure values are in millibars.

EXAMPLE 1

Production of 9-(2-fluoro-4-chloro-5-isopropyloxyphenyl)8,10-dioxo-4,1,7,9-thiatriazabicyclo[5.3.0]decane-4,4-dioxide

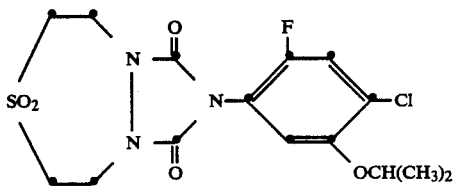

A solution of 45.0 g (0.195 mol) of 2-fluoro-4-chloro-5-isopropyloxy-phenylisocyanate in 50 ml of toluene is added dropwise at 10° C. to a solution of 20.5 g (0.195 mol) of hydrazinecarboxylic acid ethyl ester in 200 ml of toluene. After one hour, the formed precipitate is filtered off, and this is treated with 250 ml of 4 N sodium hydroxide solution. The temperature is raised to 60° C. and a clear yellow solution is obtained. On acidifying this to pH 1 with concentrated hydrochloric acid, a white precipitate is formed. After one hour's stirring at 60° C., filtration is performed and the residue is dried over phosphorus pentoxide. The yield is 52.5 g (93.9% of theory) of 4-(2-fluoro-4-chloro-5-isopropyloxyphenyl)-urazole having a melting point of 193°–194° C.

17.5 g (0.061 mol) of the above urazole are dissolved in 300 ml of ethanol. After the addition of 7.2 g (0.061 mol) of divinyl sulfone and 0.5 ml of a 6 N sodium hydroxide solution, the reaction mixture is refluxed for 8 hours, the product commencing to precipitate after about 1 hour. The yield is thus 23.0 g (92.7% of theory) of 9-(2-fluoro-4-chloro-5-isopropyloxy-phenyl-8,10-dioxo-4,1,7,9-thiatriazabicyclo[5.3.0]decane-4,4-dioxide having a melting point of 195°–196° C.

EXAMPLE 2

Production of 9-(2-fluoro-4-chloro-4-difluoromethoxyphenyl)8,10-dioxo-4,1,7,9-thiatriazabicyclo[5.3.0]decane-4,4-dioxide

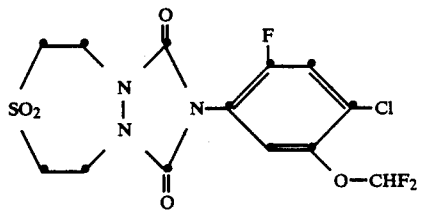

To a mixture, heated to 50° C., of 5.75 g (0.02 mol) of 4-(2-fluoro-4-chloro-5-difluoromethoxyurazole and 100 ml of ethanol are added 4 drops of 6 N KOH and 2.36 g (0.02 mol) of divinyl sulfone. Stirring is maintained until everything has gone into solution, and the solution is then refluxed for 8 hours. After it has cooled, the substance which has precipitated is filtered off with suction and dried in vacuo. The yield is 6.9 g of 9-(2-fluoro-4-chloro-5-difluoromethoxyphenyl)-8,10-dioxo-4,1,7,9-thiatriazabicyclo[5.3.0]decane-4,4-dioxide, which has a melting point of 195°–196° C.

EXAMPLE 3

Production of 9-(2-fluoro-4-chloro-5-aminophenyl)-8,10-dioxo-4,1,7,9-thiadiazabicyclo[5.3.0]decane-4,4-dioxide

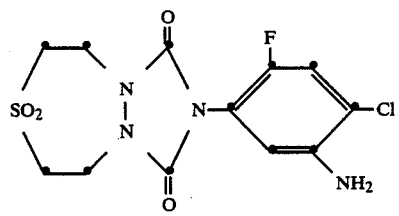

Hydrogen is introduced into a mixture of 15 g of 9-(2-fluoro-4-chloro-5-nitrophenyl)-8,10-dioxo-4,1,7,9-thiadiazabicyclo[5.3.0]decane-4,4-dioxide, 3 g of Raney nickel, 300 ml of tetrahydrofuran and 150 ml of dimethylformamide at 20°–25° C. and under normal pressure until the stoichiometric amount has been absorbed. After completion of the reaction, the catalyst is filtered off, and the filtrate is concentrated in vacuo. The residue consists of 11.6 g of 9-(2-fluoro-4-chloro-5-aminophenyl)-8,10-dioxo-4,1,7,9-thiadiazabicyclo[5.3.0]decane-4,4-dioxide having a melting point of 219°–220° C.

The 9-(2-fluoro-4-chloro-5-nitrophenyl)-8,10-dioxo-4,1,7,9-thiadiazabicyclo[5.3.0]decane-4,4-dioxide required as starting material is obtained as follows:

a) 19.1 g of 9-(2-fluoro-4-chlorophenyl)-8,10-dioxo-4,1,7,9-thiatriazabicyclo[5.3.0]decane-4,4-dioxide are added in small portions to 125 ml of concentrated sulfuric acid, which is being stirred at 0° C. To this solution are then added dropwise at 0° C., with stirring, 2.5 ml of fuming nitric acid. After being stirred for one hour at room temperature, the reaction mixture is poured onto ice, and the substance which precipitates is filtered off under suction. It is washed with water and dried to thus yield 18 g of 9-(2-fluoro-4-chloro-5-nitrophenyl)-8,10-dioxo-4,1,7,9-thiatriazabicyclo-[5.3.0]decane-4,4-dioxide having a melting point of 251°–252° C.

EXAMPLE 4

Production of 9-(2-fluoro-4-chloro-5-hydroxycarbonylmethylthio-phenyl)-8,10-dioxo-4,1,7,9-thiatriazabicyclo-[5.3.0]decanedione

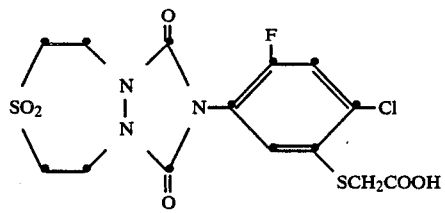

To a mixture of 17 g (0.047 mol) of 9-(5-amino-2-fluoro-4-chlorophenyl)-8,10-dione-4,1,7,9-thia-triazabicyclo[5.3.0]-decanedione (Example 3) in 25 ml of conc. hydrochloric acid and 130 ml of water, there is added slowly at a temperature of 0°–5° C., with slow stirring, under the surface, a solution of 3.9 g (0.0565 mol) of sodium nitrite in 15 ml of water. After everything has been added, stirring is continued for half an hour at this temperature; then there is added aminosulfonic acid ($H_2NSO_3H$) in order to bind the excess nitrite and subsequently a mixture of 5.5 g of thioglycolic acid (0.06 mol) and 3.1 g of basic copper carbonate (2 $CuCO_3.Cu(OH_2)$) in 50 ml of water. The mixture is stirred for two hours at room temperature. The mixture is then extracted with ethyl acetate. The extracts are washed with water and saturated salt solution dried, and concentrated by evaporation. The residue thus yields 11.6 g of the title product.

The compounds listed in the following Tables are produced in a manner corresponding to that of these Examples.

TABLE 1

| No. | Q | T | Z | |
|---|---|---|---|---|
| 1001 | F | Cl | $OCH(CH_3)_2$ | m.p. 195–196° |
| 1002 | F | Cl | $OCH_3$ | m.p. 212–214° |
| 1003 | F | Cl | $OC_2H_5$ | |
| 1004 | F | Cl | $OC_3H_7n$ | |
| 1005 | F | Cl | $OC_4H_9n$ | |
| 1006 | F | Cl | $OCH_2CH(CH_3)_2$ | |
| 1007 | F | Cl | $OCH(CH_3)C_2H_5$ | |
| 1008 | F | Cl | $OC(CH_3)_3$ | |
| 1009 | F | Br | $OCH(CH_3)_2$ | |
| 1010 | F | Br | $OCH_3$ | |
| 1011 | F | Cl | $OCH_2CH=CH_2$ | |
| 1012 | F | Cl | $OCH_2C(CH_3)=CH_2$ | |
| 1013 | F | Cl | $OCH_2C\equiv CH$ | m.p. 224–226° |
| 1014 | H | Cl | $OC_3H_7n$ | |
| 1015 | H | Br | $OC_4H_9n$ | |
| 1016 | F | Cl | OH | m.p. >300° |
| 1017 | F | Cl | $SCH_3$ | |
| 1018 | F | Cl | $SC_2H_5$ | |
| 1019 | F | Cl | $SCH(CH_3)_2$ | |
| 1020 | F | Cl | $SC_3H_7n$ | |
| 1021 | F | Cl | $SC_4H_9n$ | |
| 1022 | F | Cl | SH | |
| 1023 | F | Cl | $N(CH_3)_2$ | |
| 1024 | F | Cl | $NHCH_3$ | |

TABLE 1-continued

| No. | Q | T | Z | |
|---|---|---|---|---|
| 1025 | F | Cl | $N(CH_3)CH(CH_3)_2$ | |
| 1026 | F | Br | $N(CH_3)_2$ | |
| 1027 | F | Cl | $NH_2$ | |
| 1028 | H | Cl | $COOCH(CH_3)_2$ | |
| 1029 | H | Cl | $COOC_3H_7n$ | |
| 1030 | H | Cl | $COOCH_3$ | |
| 1031 | H | Cl | $COOC_2H_5$ | |
| 1032 | H | Cl | $COSCH_3$ | |
| 1033 | H | Cl | $COSC_2H_5$ | |
| 1034 | H | Cl | $COSC_3H_7n$ | |
| 1035 | H | Br | $COOCH(CH_3)_2$ | |
| 1036 | H | Br | $COOC_3H_7n$ | |
| 1037 | F | Br | $COSC_2H_5$ | |
| 1038 | H | Cl | $COOCH_2CH=CH_2$ | |
| 1039 | F | Br | $COOCH_2CH=CH_2$ | |
| 1040 | F | Cl | $COOCH(CH_3)_2$ | |
| 1041 | F | F | $COOCH(CH_3)_2$ | |
| 1042 | F | Cl | $COOCH_3$ | |
| 1043 | F | Cl | $COOC_2H_5$ | |
| 1044 | F | Cl | $COOC_3H_7n$ | |
| 1045 | F | Cl | $COSCH_3$ | |
| 1046 | F | Cl | $COSC_2H_5$ | |
| 1047 | F | Cl | $COSC_3H_7n$ | |
| 1048 | F | Cl | $COSCH(CH_3)_2$ | |
| 1049 | F | Cl | $COSC_4H_9n$ | |
| 1050 | F | F | $COOCH_3$ | |
| 1051 | F | Br | $COOCH(CH_3)_2$ | m.p. >212° |
| 1052 | F | Br | $COOCH_3$ | m.p. 208–210° |
| 1053 | F | Br | COOH | m.p. >250° |

TABLE 2

| No. | Q | T | Z | |
|---|---|---|---|---|
| 2.001 | F | Cl | $OCHF_2$ | m.p. 232–234° |
| 2.002 | F | Cl | $OCF_2CHClF$ | |
| 2.003 | F | Cl | $OCH_2CCl=CH_2$ | m.p. 160–161° |
| 2.004 | F | Cl | $OCF_3$ | |
| 2.005 | F | Cl | $SCF_3$ | |
| 2.006 | F | Cl | $SCHF_2$ | |
| 2.007 | F | Cl | $OCF_2CHF_2$ | m.p. 225–227° |
| 2.008 | F | Cl | $OCCl=CHCl$ | m.p. 187–190° |
| 2.009 | F | Cl | $OCH_2\equiv Cl$ | |
| 2.010 | F | Cl | $OCH_2CCl=CHCl$ | |
| 2.011 | F | Cl | $OCH(CH_3)CH_2Cl$ | |
| 2.012 | F | Cl | $OCH_2CH_2F$ | |
| 2.013 | F | Cl | $OCH_2CH_2Cl$ | |
| 2.014 | F | Cl | $OCH_2CH_2Br$ | |
| 2.015 | F | Cl | $OCH_2CH_2I$ | |
| 2.016 | F | Cl | $OCF_2CHFCF_3$ | m.p. 144–147° |
| 2.017 | F | Cl | $OCF_2CHCl_2$ | |
| 2.018 | F | Cl | $OCF_2CF_3$ | m.p. 205–207° |
| 2.019 | F | Cl | $OCClF_2$ | |
| 2.020 | H | Br | $OCF_3$ | |
| 2.021 | H | Cl | $OCHF_2$ | |
| 2.022 | H | Cl | $OCH_2CCl=CH_2$ | |
| 2.023 | H | Br | $OCHCCl=CH_2$ | |
| 2.024 | H | Cl | $OCF_2CF_3$ | |
| 2.025 | H | Br | $OCF_2CF_3$ | |

TABLE 2-continued

Structure: ring with CH₂-CH₂-SO₂-CH₂-CH₂ connected to N-N, with two C=O groups, attached to phenyl ring with Q, T, Z substituents.

| No. | Q | T | Z |
|---|---|---|---|
| 2.026 | H | Cl | SCF₃ |
| 2.027 | H | Br | SCF₃ |
| 2.028 | H | Cl | OCH(CH₃)CH₂Cl |
| 2.029 | H | Br | OCH(CH₃)CH₂Cl |
| 2.030 | H | Cl | OCH(CH₃)CH₂Cl |

TABLE 3

| No. | Q | T | Z |
|---|---|---|---|
| 3.001 | F | Cl | COOCH₂COOCH₃ |
| 3.002 | F | Cl | COOCH₂COOC₂H₅ |
| 3.003 | F | Cl | COOCH₂COOCH(CH₃)₂ |
| 3.004 | F | Cl | COOCH(CH₃)COOCH₃ |
| 3.005 | F | Cl | COOCH(CH₃)COOC₂H₅ |
| 3.006 | F | Cl | COOCH(CH₃)COOC₃H₇-n |
| 3.007 | F | Cl | COOCH(CH₃)COOCH(CH₃)₂ |
| 3.008 | F | Cl | COOCH(CH₃)COOC₄H₉-n |
| 3.009 | F | Cl | COOCH(CH₃)COOCH₂CH(CH₃)₂ |
| 3.010 | F | Cl | COOCH(CH₃)COOCH(CH₃)C₂H₅ |
| 3.011 | F | Cl | COSCH₂COOCH₃ |
| 3.012 | F | Cl | COSCH₂COOC₂H₅ |
| 3.013 | F | Cl | COSCH₂COOC₃H₇-n |
| 3.014 | F | Cl | COSCH₂COOCH(CH₃)₂ |
| 3.015 | F | Cl | COSCH₂COOCH₂CH=CH₂ |
| 3.016 | F | Cl | COSCH₂COOcyclohexyl |
| 3.017 | F | Cl | COSCH₂COOC₄H₉-n |
| 3.018 | F | Cl | COSCH(CH₃)COOCH₃ |
| 3.019 | F | Cl | COSCH(CH₃)COOC₂H₅ |
| 3.020 | F | Cl | COSCH(CH₃)COOC₃H₇-n |
| 3.021 | F | Cl | COSCH(CH₃)COOCH(CH₃)₂ |
| 3.022 | F | Cl | COSCH(CH₃)COOC₄H₉-n |
| 3.023 | F | Cl | COSCH(CH₃)COOCH₂CH(CH₃)₂ |
| 3.024 | F | Cl | COSCH(CH₃)COOCH(CH₃)C₂H₅ |
| 3.025 | F | Cl | COSCH(CH₃)COOC(CH₃)₂ |
| 3.026 | F | Cl | COSCH(CH₃)COOCH₂CH=CH₂ |
| 3.027 | F | Cl | COSCH(CH₃)COOCHC≡CH |
| 3.028 | F | Cl | COSCH(CH₃)COOcyclohexyl |
| 3.029 | H | Cl | COOCH₂COOCH₃ |
| 3.030 | H | Cl | COOCH₂COOC₂H₅ |
| 3.031 | H | Cl | COOCH₂COOC₃H₇-n |
| 3.032 | H | Cl | COOCH₂COOCH(CH₃)₂ |
| 3.033 | H | Cl | COOCH(CH₃)COOCH₃ |
| 3.034 | H | Cl | COOCH(CH₃)COOC₂H₅ |
| 3.035 | H | Cl | COOCH(CH₃)COOC₃H₇-n |
| 3.036 | H | Cl | COOCH(CH₃)COOCH(CH₃)₂ |
| 3.037 | H | Cl | COOCH(CH₃)COOC₄H₉-n |
| 3.038 | H | Cl | COOCH(CH₃)COOCH₂CH(CH₃)₂ |
| 3.039 | H | Cl | COOCH(CH₃)COOCH(CH₃)C₂H₅ |
| 3.040 | H | Cl | COOCH(CH₃)COOC(CH₃)₂ |
| 3.041 | H | Cl | COSCH₂COOCH₃ |
| 3.042 | H | Cl | COSCH₂COOC₂H₅ |
| 3.043 | H | Cl | COSCH₂COOC₃H₇-n |
| 3.044 | H | Cl | COSCH₂COOCH(CH₃)₂ |
| 3.045 | H | Cl | COSCH₂COOCH₂CH=CH₂ |
| 3.046 | H | Cl | COSCH₂COOcyclohexyl |
| 3.047 | H | Cl | COSCH₂COOC₄H₉-n |
| 3.048 | H | Cl | COSCH(CH₃)COOCH₃ |

TABLE 3-continued

| No. | Q | T | Z |
|---|---|---|---|
| 3.049 | H | Cl | COSCH(CH₃)COOC₂H₅ |
| 3.050 | H | Cl | COSCH(CH₃)COOC₃H₇-n |
| 3.051 | H | Cl | COSCH(CH₃)COOCH(CH₃)₂ |
| 3.052 | H | Cl | COSCH(CH₃)COOC₄H₉-n |
| 3.053 | H | Cl | COSCH(CH₃)COOCH₂CH(CH₃)₂ |
| 3.054 | H | Cl | COSCH(CH₃)COOCH(CH₃)C₂H₅ |
| 3.055 | H | Cl | COSCH(CH₃)COOC(CH₃)₂ |
| 3.056 | H | Cl | COSCH(CH₃)COOCH₂CH=CH₂ |
| 3.057 | H | Cl | COSCH(CH₃)COOCH₂C≡CH |
| 3.058 | H | Cl | COSCH(CH₃)COOcyclohexyl |
| 3.059 | F | Br | COOCH₂COOCH₃ |
| 3.060 | F | Br | COOCH₂COOC₂H₅ |
| 3.061 | F | Br | COOCH(CH₃)COOCH₃ |
| 3.062 | F | Br | COOCH(CH₃)COOCH(CH₃)₂ |
| 3.063 | F | Br | COOCH(CH₃)COOC₂H₅ |
| 3.064 | F | Br | COOCH(CH₃)COOCH₂CH=CH₂ |
| 3.065 | F | Br | COSCH₂COOCH₃ |
| 3.066 | F | Br | COSCH(CH₃)COOCH₃ |
| 3.067 | F | Br | COSCH(CH₃)COOC₂H₅ |
| 3.068 | F | Br | COSCH₂COOCH(CH₃)₂ |
| 3.069 | F | Br | COSCH(CH₃)COOCH₂CH=CH₂ |
| 3.070 | F | Br | COSCH(CH₃)COOcyclohexyl |

TABLE 4

| No. | Q | T | Z | |
|---|---|---|---|---|
| 4.001 | F | Cl | OCH₂COOH | |
| 4.002 | F | Cl | OCH₂COOCH₃ | |
| 4.003 | F | Cl | OCH₂COOC₂H₅ | |
| 4.004 | F | Cl | OCH₂COOC₃H₇-n | |
| 4.005 | F | Cl | OCH₂COOCH(CH₃)₂ | |
| 4.006 | F | Cl | OCH₂COOC₄H₉-n | |
| 4.007 | F | Cl | OCH₂COOCH₂CH(CH₃)₂ | |
| 4.008 | F | Cl | OCH₂COOCH(CH₃)C₂H₅ | |
| 4.009 | F | Cl | OCH₂COOC(CH₃)₃ | |
| 4.010 | F | Cl | OCH₂COOcyclohexyl | |
| 4.011 | F | Cl | OCH₂COOcyclopentyl | |
| 4.012 | F | Cl | OCH₂COOCH₂CH=CH₂ | |
| 4.013 | G | Cl | OCH₂COOCH₂C≡CH | |
| 4.014 | F | Cl | OCH₂COOCH₂CH₂Cl | |
| 4.015 | F | Cl | OCH₂COOCH₂CH₂OCH₃ | |
| 4.016 | F | Cl | OCH₂COOCH₂CCl=CH₂ | |
| 4.017 | F | Cl | OCH(CH₃)COOH | |
| 4.018 | F | Cl | OCH(CH₃)COOCH₃ | m.p. 185–186° |
| 4.019 | F | Cl | OCH(CH₃)COOC₂H₅ | |
| 4.020 | F | Cl | OCH(CH₃)COOC₃H₇-n | |
| 4.021 | F | Cl | OCH(CH₃)COOCH(CH₃)₂ | |
| 4.022 | F | Cl | OCH(CH₃)COOC₄H₉-n | |
| 4.023 | F | Cl | OCH(CH₃)COOCH₂CH(CH₃)₂ | |
| 4.024 | F | Cl | OCH(CH₃)COOCH(CH₃)C₂H₅ | |
| 4.025 | F | Cl | OCH(CH₃)COOC(CH₃)₃ | |
| 4.026 | F | Cl | OCH(CH₃)COOcyclohexyl | |
| 4.027 | F | Cl | OCH(CH₃)COOcyclopentyl | |
| 4.028 | F | Cl | OCH(CH₃)COOCH₂CH=CH₂ | |
| 4.029 | F | Cl | OCH(CH₃)COOCH₂C≡CH | |
| 4.030 | F | Cl | OCH(CH₃)COOCH₂CH₂Cl | |

TABLE 4-continued

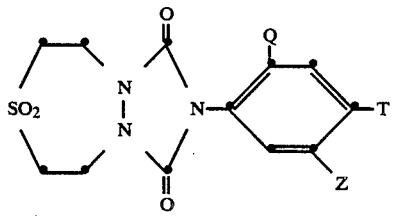

| No. | Q | T | Z |
|---|---|---|---|
| 4.031 | F | Cl | OCH(CH$_3$)COOCH$_2$CH$_2$OCH$_3$ |
| 4.032 | F | Cl | OCH(CH$_3$)COOCH$_2$CCl=CH$_2$ |
| 4.033 | F | Br | OCH$_2$COOH |
| 4.034 | F | Br | OCH$_2$COOCH$_3$ |
| 4.035 | F | Br | OCH$_2$COOC$_2$H$_5$ |
| 4.036 | F | Br | OCH$_2$COOCH(CH$_3$)$_2$ |
| 4.037 | F | Br | OCH$_2$COOC$_4$H$_9$-n |
| 4.038 | F | Br | OCH$_2$COOCH$_2$CH=CH$_2$ |
| 4.039 | F | Br | OCH(CH$_3$)COOH |
| 4.040 | F | Br | OCH(CH$_3$)COOCH$_3$ |
| 4.041 | F | Br | OCH(CH$_3$)COOC$_2$H$_5$ |
| 4.042 | F | Br | OCH(CH$_3$)COOCH(CH$_3$)$_2$ |
| 4.043 | F | Br | OCH(CH$_3$)COOC$_4$H$_9$-n |
| 4.044 | F | Br | OCH(CH$_3$)COOCH$_2$CH=CH$_2$ |
| 4.045 | F | Br | OCH(CH$_3$)COOcyclopentyl |
| 4.046 | F | Br | OCH(C$_2$H$_5$)COOH |
| 4.047 | F | Br | OCH(C$_2$H$_5$)COOCH$_3$ |
| 4.048 | F | Br | OCH(C$_2$H$_5$)COOC$_2$H$_5$ |
| 4.049 | F | Br | OCH(C$_2$H$_5$)COOCH(CH$_3$)$_2$ |
| 4.050 | F | Br | OCH(C$_2$H$_5$)COOC$_4$H$_9$-n |
| 4.051 | F | Br | OCH(C$_2$H$_5$)COOCH$_2$CH=CH$_2$ |
| 4.052 | F | Br | OCH(C$_2$H$_5$)COOcyclohexyl |

TABLE 5

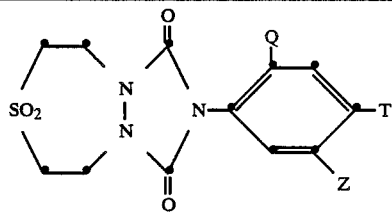

| No. | Q | T | Z | |
|---|---|---|---|---|
| 5.001 | F | Cl | SCH$_2$COOH | |
| 5.002 | F | Cl | SCH$_2$COOCH$_3$ | |
| 5.003 | F | Cl | SCH$_2$COOC$_2$H$_5$ | m.p. 101° d. |
| 5.004 | F | Cl | SCH$_2$COOC$_3$H$_7$-n | |
| 5.005 | F | Cl | SCH$_2$COOCH(CH$_3$)$_2$ | |
| 5.006 | F | Cl | SCH$_2$COOC$_4$H$_9$-n | |
| 5.007 | F | Cl | SCH$_2$COOCH$_2$CH(CH$_3$)$_2$ | |
| 5.008 | F | Cl | SCH$_2$COOCH$_2$CH(CH$_3$)C$_2$H$_5$ | |
| 5.009 | F | Cl | SCH$_2$COOC(CH$_3$)$_3$ | |
| 5.010 | F | Cl | SCH$_2$COOcyclohexyl | |
| 5.011 | F | Cl | SCH$_2$COOcyclopentyl | |
| 5.012 | F | Cl | SCH$_2$COOCH$_2$CH=CH$_2$ | |
| 5.013 | F | Cl | SCH$_2$COOCH$_2$C≡CH | |
| 5.014 | F | Cl | SCH$_2$COOCH$_2$CH$_2$Cl | |
| 5.015 | F | Cl | SCH$_2$COOCH$_2$CH$_2$OCH$_3$ | |
| 5.016 | F | Cl | SCH$_2$COOCH$_2$CCl=CH$_2$ | |
| 5.017 | F | Cl | SCH(CH$_3$)COOH | |
| 5.018 | F | Cl | SCH(CH$_3$)COOCH$_3$ | |
| 5.019 | F | Cl | SCH(CH$_3$)COOC$_2$H$_5$ | |
| 5.020 | F | Cl | SCH(CH$_3$)COOC$_3$H$_7$-n | |
| 5.021 | F | Cl | SCH(CH$_3$)COOCH(CH$_3$)$_2$ | |
| 5.022 | F | Cl | SCH(CH$_3$)COOC$_4$H$_9$-n | |
| 5.023 | F | Cl | SCH(CH$_3$)COOCH$_2$CH(CH$_3$)$_2$ | |
| 5.024 | F | Cl | SCH(CH$_3$)COOCH$_2$CH(CH$_3$)C$_2$H$_5$ | |
| 5.025 | F | Cl | SCH(CH$_3$)COOC(CH$_3$)$_3$ | |
| 5.026 | F | Cl | SCH(CH$_3$)COOcyclohexyl | |
| 5.027 | F | Cl | SCH(CH$_3$)COOcyclopentyl | |
| 5.028 | F | Cl | SCH(CH$_3$)COOCH$_2$CH=CH$_2$ | |
| 5.029 | F | Cl | SCH(CH$_3$)COOCH$_2$C≡CH | |
| 5.030 | F | Cl | SCH(CH$_3$)COOCH$_2$CH$_2$Cl | |
| 5.031 | F | Cl | SCH(CH$_3$)COOCH$_2$CH$_2$OCH$_3$ | |

TABLE 5-continued

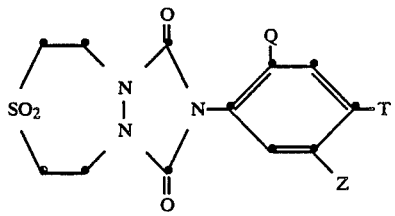

| No. | Q | T | Z |
|---|---|---|---|
| 5.032 | F | Cl | SCH(CH$_3$)COOCH$_2$CCl=CH$_2$ |
| 5.033 | F | Br | SCH$_2$COOH |
| 5.034 | F | Br | SCH$_2$COOCH$_3$ |
| 5.035 | F | Br | SCH$_2$COOC$_2$H$_5$ |
| 5.036 | F | Br | SCH$_2$COOCH(CH$_3$)$_2$ |
| 5.037 | F | Br | SCH$_2$COOC$_4$H$_9$-n |
| 5.038 | F | Br | SCH$_2$COOCH$_2$CH=CH$_2$ |
| 5.039 | F | Br | SCH(CH$_3$)COOH |
| 5.040 | F | Br | SCH(CH$_3$)COOCH$_3$ |
| 5.041 | F | Br | SCH(CH$_3$)COOC$_2$H$_5$ |
| 5.042 | F | Br | SCH(CH$_3$)COOCH(CH$_3$)$_2$ |
| 5.043 | F | Br | SCH(CH$_3$)COOC$_4$H$_9$-n |
| 5.044 | F | Br | SCH(CH$_3$)COOCH$_2$CH=CH$_2$ |
| 5.045 | F | Br | SCH(CH$_3$)COOcyclopentyl |
| 5.046 | F | Br | SCH(C$_2$H$_5$)COOH |
| 5.047 | F | Br | SCH(C$_2$H$_5$)COOCH$_3$ |
| 5.048 | F | Br | SCH(C$_2$H$_5$)COOC$_2$H$_5$ |
| 5.049 | F | Br | SCH(C$_2$H$_5$)COOCH(CH$_3$)$_2$ |
| 5.050 | F | Br | SCH(C$_2$H$_5$)COOC$_4$H$_9$-n |
| 5.051 | F | Br | SCH(C$_2$H$_5$)COOCH$_2$CH=CH$_2$ |
| 5.052 | F | Br | SCH(C$_2$H$_5$)COOcyclohexyl |

FORMULATION EXAMPLES

Example 5

Formulation Examples for active ingredients of the formula I (%=per cent by weight)

| (a) Wettable powders | (a) | (b) | (c) |
|---|---|---|---|
| active ingredient according to Tables 1 to 5 | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7-8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and the mixture is ground in a suitable mill. These are thus obtained wettable powders which can be diluted with water to give suspensions of the concentration required.

| (b) Emulsion concentrates | (a) | (b) |
|---|---|---|
| active ingredient according to Tables 1 to 5 | 10% | 1% |
| octylphenolpolyethylene glycol ether (4-5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentrations required can be obtained from these concentrates by diluted with water.

| (c) Dusts | (a) | (b) |
|---|---|---|
| active ingredient according to Tables 1 to 5 | 0.1% | 1% |
| talcum | 99.9% | — |
| kaolin | — | 99% |

Dusts ready for use are obtained by mixing the active ingredient with the carriers, and grinding the mixture in a suitable mill.

| (d) Extruder granulates | (a) | (b) |
|---|---|---|
| active ingredient according to Tables 1 to 5 | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granulate | |
|---|---|
| active ingredient according to Tables 1 to 5 | 3% |
| polyethylene glycol (M.W. 200) | 3% |
| kaolin | 94% |

The finely ground active ingredient is uniformly applied in a mixer to the kaolin moistened with polyethylene glycol. Non-dusty coated granulates are obtained in this manner.

| (f) Suspension concentrates | (a) | (b) |
|---|---|---|
| active ingredient according to Tables 1 to 5 | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is thus obtained a suspension concentrate from which can be produced, by dilution with water, suspensions of the concentration required.

| (g) Salt solution | |
|---|---|
| active ingredient according to Tables 1 to 5 | 5% |
| isopropylamine | 1% |
| octylphenolpolyethylene glycol ether (78 mols of ethylene oxide) | 3% |
| water | 91% |

BIOLOGICAL EXAMPLES

Example 6: Pre-emergence herbicidal action

Immediately after the sowing of the test plants in trays in a greenhouse, the surface of the soil is sprayed with an aqueous dispersion of the active ingredient, the dispersion having been obtained from a 25% emulsion concentrate. Concentrations corresponding to 4 kg of active ingredient per hectare are used. The seed trays are kept in a greenhouse at 22°-25° C. with 50-70% relative humidity; the test is concluded after 3 weeks and the results are then assessed on the basis of the following scale of ratings:

1=plant has not germinated or has died,
2-3=very severe damage,
4=severe damage,
5=moderate damage, the plants have become stunted,
6=damage, but the plant can regenerate,
7-8=slight damage,
9=normal growth, as in the case of the untreated plants.

The results are summarised below.

The compound A is the 9-(2,5-diethoxyphenyl)-8,10-dioxo-4,1,7,9-thiatriazabicyclo[5.3.0]decane-4,4-dioxide known from the German Offenlegungsschrift No. 2,638,543.

| Compound | Avena sativa | Sinapis alba | Setaria italica | Sellaria media |
|---|---|---|---|---|
| 1.001 | 1 | 1 | 1 | 1 |
| A | 9 | 9 | 9 | 9 |

Example 7: Post-emergence herbicidal action (contact herbicide)

A number of weeds, both monocotyledonous and dicotyledonous, are sprayed after emergence (in the 4- to 6-leaf stage) with an aqueous active-ingredient dispersion at a dosage level corresponding to 4 kg of active ingredient per hectare, and the treated plants are kept at 24°-26° C. with 45-60% relative humidity. Fifteen days after the treatment, the test results are evaluated on the basis of the above scale of ratings. These results are summarised below.

| Plant | Compound 1.001 | A |
|---|---|---|
| Avena fatua | 1 | 9 |
| Setaria italica | 1 | 9 |
| Lolium perenne | 1 | 9 |
| Sotanum lycopers. | 1 | 9 |
| Sinapis alba | 1 | 7 |
| Stellaria media | 2 | 9 |
| Phaseolus vulgaris | 1 | 8 |

Example 8: Herbicidal action before emergence of the plants

Plastics pots are filled with expanded vermiculite (density: 0.135 g/cm$^3$, water-absorption capacity: 0.565 l/l). After saturation of the non-adsorptive vermiculite with an aqueous active-ingredient emulsion in deionised water, which contains the active ingredient at a concentration of 70.8 ppm, seeds of the following plants are sown on the surface: *Nasturtium officinalis, Agrostis tenuis, Stellaria media* and *Digitaria sanguinalis*. The test vessels are subsequently kept in a climatic chamber at 20° C., with an illumination of about 20 k lux and a relative humidity of 70%. During the germination phase of 4 to 6 days, the pots are covered over with a light-permeable material in order to raise the local air humidity and watered with deionised water. After the 5th day, 0.5% of a commercial liquid fertiliser (®

Greenzit) is added to the water. The test is evaluated 12 days after sowing, and the effect on the test plants is assessed.

The tested compounds of the Tables 1 to 5 exhibit in this test a good to very good herbicidal action.

Example 9: Herbicidal action in the case of paddy rice

The water weeds *Echinochloa crus galli* and *Monocharia vag.* are sown in plastic containers (60 cm² surface area, 500 ml volume). After the sowing of the seeds, water is added until it is up to the level of the soil; and three days after sowing, the level of water is raised to slightly above the soil level (3–5 mm). Application of an aqueous emulsion of the test substance is made, by spraying of the containers, three days after sowing. The applied dose corresponds to an active-substance amount of 0.5 to 4 kg per hectare (amount of spray liquor=550 liters per hectare). The plant containers are then kept in a greenhouse under optimum growth conditions for the rice weeds, that is, at 25°–30° C. with high relative humidity. The assessment of the test results is made three weeks after application of the test substance.

The compounds listed in Tables 1 to 5 attack and destroy the weeds but not the rice.

Example 10: Reduction in growth of tropical leguminous cover crops

The test plants (*Centrosema plumieri* and *Centrosema pubescens*) are cultivated to the fully grown stage, and are then cut back to a height of 60 cm. After seven days, the active ingredient is sprayed on in the form of an aqueous emulsion. The test plants are maintained at 70% relative humidity and with 6000 lux of artificial light, 14 hours per day, at a temperature of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients from Tables 1 to 5, in an applied amount of 50–3000 g per hectare, show in this test a clear reduction in new growth (less than 20% of the new growth occurring on untreated control plants), without the test plants having suffered damage.

Example 11: Regulation of the growth of soya beans

Soya beans of the "Hark" variety are sown in a soil/peat/sand mixture (6:3:1) in plastics containers and these are placed in a controlled-atmosphere chamber. By virtue of optimum choice of temperature, illumination, supply of fertiliser and watering, the plants are able to develop during about five weeks to the 5–6 trifoliate leaf-stage. The plants at this point of time are sprayed with the aqueous spray liquor of an active ingredient of the formula I until they are fully wetted. The active-ingredient concentration is up to 100 g of active ingredient per hectare. An evaluation is made about five weeks after application of the spray liquor.

The active substances in Tables 1 to 5 effect a marked increase in the number and weight of the pods in the leading shoots compared with those measured on the untreated control plants.

Example 12: Reduction in the growth of cereals

The cereal varieties *Hordeum vulgare* (spring barley) and *Secale* (spring rye) are sown in plastics pots containing sterilised soil in a greenhouse, and watered as required. The young shoots are sprayed, about 21 days after sowing, with the aqueous spray liquor of an active ingredient from Tables 1 to 5. The amount of active ingredient is equivalent to up to 100 g per hectare. An assessment of the growth of the cereals is made 21 days after application.

The treated plants show a reduction of new growth (60–90% of that of control plants), and also in some cases an increase in the diameter of the stalks.

Example 13: Reduction in the growth of grasses

The grasses *Lolium perenne, Poa pratensis, Festuca ovina, Dactylis glomerate* and *Cynodon dactylon* are sown, in a greenhouse, in plastics dishes containing a soil/peat/sand mixture (6:3:1), and watered as required. The emerged grasses are cut back weekly to a height of about 4 cm, and are sprayed, about 50 days after sowing and one day after the final cutting, with the aqueous spray liquor of an active ingredient from Tables 1 to 5. The amount of active ingredient corresponds, when converted, to up to 500 g per hectare. The growth of the grasses is assessed 21 days after application of the spray liquor.

The tested compounds of Tables 1 to 5 effect a reduction on new growth of around 10–30% compared with the new growth on the control plants.

Example 14: Desiccating and defoliating action

Cotton plants of the Deltapine variety are grown in clay pots in a greenhouse. After the bolls have finished forming, the plants are sprayed with aqueous preparations of the active ingredient in amounts equivalent to 1.2, 0.6 and 0.3 kg per hectare in the field. Untreated plants are used as control specimens. An evaluation of the test is made 3, 7 and 14 days after application of the test substance by determining the degree of defoliation (% of leaves which have fallen) and of desiccation (% drying out of the leaves remaining on the plant).

In this test, the compounds of Tables 1 to 5 in applied amounts of 0.6 and 1.2 kg/hectare, respectively, left after 7 days just a very few dried up leaves on the plants (more than 80% leaf-fall and desiccation).

What is claimed is:

1. An annularly-linked triazole compound of the formula I

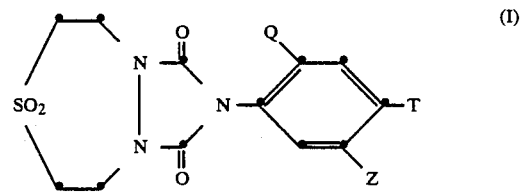

wherein
Q is fluorine,
T is chlorine or bromine,
Z is a radical —XR,
X is oxygen or sulfur,
R is a $C_2$–$C_6$-alkenyl or $C_3$–$C_6$-alkynyl radical, which is unsubstituted or substituted by halogen, or is a radical —A—$COXR_1$, in which
A is a $C_1$–$C_4$-alkylene bridge and
$R_1$ is $C_1$–$C_4$-alkyl.

2. A compound according to claim 1 of the formula I wherein
X is oxygen,

R is a $C_2$–$C_6$-alkenyl or $C_3$–$C_6$-alkynyl radical, which is unsubstituted or substituted by halogen.

3. A compound according to claim 1 of the formula I wherein

R is a radical —A—$COXR_1$.

4. 9-(2-Fluoro-4-chloro-5-propynyloxyphenyl)-8,10-dioxo-4,1,7,9-thiatriazabicyclo[5.3.0]decane-4,4-dioxide according to claim 1.

5. 9-[2-Fluoro-4-chloro-5-(2'-chloroallyloxy)phenyl]-8,10-dioxo-4,1,7,9-thiatraizabicyclo[5.3.0]-decane-4,4-dioxide according to claim 1.

6. 9-[2-Fluoro-4-chloro-5-(1',2'-dichlorovinyl)-phenyl]-8,10-dioxo-4,1,7,9-thiatriazabicyclo[5.3.0]decane-4,4-dioxide according to claim 1.

7. 9-[2-Fluoro-4-chloro-5-(methoxycarbonyleth-1-yloxy)phenyl]-8,10-dioxo-4,1,7,9-thiatriazabicyclo[5.3.0]decane-4,4-dioxide according to claim 1.

8. 9-[2-Fluoro-4-chloro-5-(ethoxycarbonylmethylthio)phenyl]-8,10-dioxo-4,1,7,9-thiatriazabicyclo[5.3.0]-decane-4,4-dioxide according to claim 1.

9. A herbicidal and plant-growth regulating composition which contains as active ingredient an effective amount of an annularly-linked triazole compound according to claim 1, together with inert carriers and/or other additives.

10. A method of selectively controlling, before or after emergence of the plants, weeds in crops of cereals, maize, rice and rape-seed, which method comprises treating said crops or the cultivated area thereof with a herbicidally effective amount of an active substance according to claim 1, or of a composition containing such a compound as active ingredient.

11. A method of suppressing plant growth beyond the 2-leaf stage, which method comprises treating the plants during their growth with a growth regulatingly effective amount of an active substance according to claim 1, or of a composition containing such a compound as active ingredient.

* * * * *